United States Patent
Kume et al.

(10) Patent No.: US 9,581,565 B2
(45) Date of Patent: Feb. 28, 2017

(54) GAS SENSOR

(71) Applicant: NGK SPARK PLUG CO., LTD., Nagoya-shi, Aichi (JP)

(72) Inventors: Makoto Kume, Inuyama (JP); Nobuhiro Inoue, Tajimi (JP); Daisuke Tahira, Komaki (JP); Shingo Ito, Ichinomiya (JP); Yuichi Yamada, Komaki (JP)

(73) Assignee: NGK SPARK PLUG CO., LTD., Aichi (JP)

(*) Notice: Subject to any disclaimer, the term of this patent is extended or adjusted under 35 U.S.C. 154(b) by 179 days.

(21) Appl. No.: 14/278,246

(22) Filed: May 15, 2014

(65) Prior Publication Data
US 2014/0338424 A1 Nov. 20, 2014

(30) Foreign Application Priority Data

May 20, 2013 (JP) .................................. 2013-106474
Nov. 20, 2013 (JP) .................................. 2013-239722

(51) Int. Cl.
*G01N 27/407* (2006.01)
*G01M 15/10* (2006.01)
*G01N 1/00* (2006.01)

(52) U.S. Cl.
CPC ...... *G01N 27/4077* (2013.01); *G01M 15/102* (2013.01); *G01N 1/00* (2013.01); *G01N 27/407* (2013.01)

(58) Field of Classification Search
CPC .......................... G01M 15/102; G01N 27/407
See application file for complete search history.

(56) References Cited

U.S. PATENT DOCUMENTS 4,019,974 A * 4/1977 Weyl .................. G01N 27/4062
204/428
4,956,072 A 9/1990 Kojima et al.
(Continued)

FOREIGN PATENT DOCUMENTS

JP 01043752 A * 2/1989
JP 1-140055 A 6/1989
(Continued)

OTHER PUBLICATIONS

Communication (Office Action) dated Dec. 21, 2015 from the Japanese Patent Office in counterpart Japanese Patent Application No. 2013-239722.
(Continued)

*Primary Examiner* — Lisa Caputo
*Assistant Examiner* — Punam Roy
(74) *Attorney, Agent, or Firm* — Sughrue Mion, PLLC

(57) ABSTRACT

Disclosed is a gas sensor having a metal shell, a holder placed in the metal shell and a sensor element inserted through an axial insertion hole of the holder. The holder has a recessed portion recessed toward the rear from a front end face of the holder. The sensor element has, at a front end part thereof, a detection portion covered with a porous protection layer such that a rear end of the porous protection layer is situated within the recessed portion of the holder and is located at the rear side with respect to the front end face of the holder while maintaining a space between an inner circumferential surface of the recessed portion and an outer circumferential surface of the porous protection layer.

3 Claims, 8 Drawing Sheets

(56) References Cited

U.S. PATENT DOCUMENTS

| | | | |
|---|---|---|---|
| 5,707,504 | A | 1/1998 | Jyouno et al. |
| 5,922,938 | A | 7/1999 | Hafele |
| 7,565,826 | B2 * | 7/2009 | Nakagawa ............ G01N 27/407 73/23.2 |
| 8,656,756 | B2 * | 2/2014 | Mizutani ............ G01N 27/4077 73/23.2 |
| 2007/0157939 | A1 * | 7/2007 | Nakagawa ............ G01N 27/407 131/346 |
| 2007/0251823 | A1 | 11/2007 | Yamada |
| 2008/0022754 | A1 | 1/2008 | Nakagawa |
| 2008/0209984 | A1 | 9/2008 | Yamada |
| 2009/0314056 | A1 | 12/2009 | McCauley et al. |
| 2009/0315268 | A1 * | 12/2009 | McCauley ............ G01N 27/407 277/313 |
| 2011/0283774 | A1 | 11/2011 | Sekiya et al. |
| 2012/0211362 | A1 | 8/2012 | Onkawa et al. |
| 2014/0260531 | A1 * | 9/2014 | Oba .................. G01N 27/4078 73/23.2 |
| 2014/0305188 | A1 * | 10/2014 | Kume ................ G01N 27/4077 73/23.2 |
| 2014/0339081 | A1 * | 11/2014 | Tahira ................ G01M 15/102 204/424 |

FOREIGN PATENT DOCUMENTS

| | | | |
|---|---|---|---|
| JP | 01140055 | A * | 6/1989 |
| JP | 5-69669 | U | 9/1993 |
| JP | 8-254521 | A | 10/1996 |
| JP | 9-512912 | A | 12/1997 |
| JP | 2004-093302 | A | 3/2004 |
| JP | 2006-343297 | A | 12/2006 |
| JP | 2007-17407 | A | 1/2007 |
| JP | 2007-316051 | A | 12/2007 |
| JP | 2008-32651 | A | 2/2008 |
| JP | 2008-145288 | A | 6/2008 |
| JP | 2009-80100 | A | 4/2009 |
| JP | 2009-115781 | A | 5/2009 |
| JP | 2010-243422 | A | 10/2010 |
| JP | 2012-002805 | A | 1/2012 |
| JP | 2012-189579 | A | 10/2012 |

OTHER PUBLICATIONS

Communication dated Aug. 16, 2016, from the Japanese Patent Office in counterpart application No. 2013-106474.

* cited by examiner

GAS SENSOR

BACKGROUND OF THE INVENTION

The present invention relates to a gas sensor (such as oxygen sensor, NOx sensor, HC sensor etc.) for detecting the concentration of a specific gas component in a gas under measurement.

Hereinafter, the term "front" refers to a gas sensing side with respect to an axial direction of a gas sensor; and the term "rear" refers to a side opposite the front side.

Japanese Laid-Open Patent Publication No. 2012-189579 discloses one type of gas sensor (e.g. oxygen gas sensor) that includes an elongated plate-shaped or rod-shaped sensor element having, at a front end part thereof, a detection portion constituted by an oxygen ion conducting solid electrolyte material and a pair of detection electrodes. In this type of gas sensor, the sensor element is held in position by a holder within a cylindrical metal shell (metal housing). The holder is formed of an insulating material (such as ceramic material e.g. alumina) with an axial through hole so that the sensor element is inserted through the axial though hole of the holder with the front end part (detection portion) of the sensor element protruding toward the front from a front end of the holder. The metal shell is equipped with a thread portion so that the gas sensor is mounted to e.g. an exhaust pipe of an internal combustion engine by screwing the thread portion into a mounting hole of the exhaust gas. In a state where the gas sensor is mounted to the engine exhaust pipe, the detection portion of the sensor element is situated inside of the exhaust pipe and exposed to an exhaust gas (as a gas under measurement) so as to generate an electric signal responsive to the concentration of a specific gas component (e.g. oxygen) in the exhaust gas. Electrode terminals are formed on a rear end part of the sensor element and connected to an ECU (engine control unit; as an external device) through leads so that the electric signal of the sensor element is outputted to the ECU for air-fuel ratio control etc.

In order to cover the front end part of the sensor element and protect the detection portion from water contained in the exhaust gas, a protector (protection cover) having a plurality of vent holes is attached to a front end of the metal shell. In addition, a protection layer of porous material (e.g. spinel or alumina) is commonly formed on a predetermined surface region from the front end of the sensor element toward the rear in order to prevent the sensor element from deteriorating in detection performance due to the adhesion of a foreign substance contained in the exhaust gas or becoming broken due to the adhesion of water contained in the exhaust gas. The formation of such a porous protection layer is particularly effective as a measure against the breakage of the sensor element caused due to thermal impact by the adhesion of water in the case where a heater is provided on the sensor element for rapid heating and activation of the solid electrolyte material.

Herein, a noble metal material (e.g. platinum or alloy thereof) is used for various conductors (conduction layers) such as detection electrodes, heater energization electrodes etc. in the above-mentioned sensor element. The amount of use of the noble metal material increases with the axial length of the sensor element, which results in a cost increase. It is demanded to reduce the axial length of the sensor element for cost reduction. In recent years, there has been a demand to reduce the axial length or size of the sensor element for the purpose of not only decreasing the amount of use of the noble metal material for cost reduction but also decreasing the power consumption of the sensor element for energy conservation.

For the length reduction of the sensor element, it is conceivable to decrease the amount (length) by which the rear end part of the sensor element protrudes toward the rear from the holder. As mentioned above, the rear end part of the sensor element is a place where the electrode terminals are formed for electrical connection to front ends of the leads by crimp contacts. It is thus necessary to secure a predetermined length of the rear end part of the sensor element in order to improve the reliability of the electrical connection. It is also necessary, in view of the fact that the detection portion of the sensor element reaches a high activation temperature, to locate the electrode terminals apart (away) from the detection portion in order to avoid the electrical connection from being influenced by heat from the detection portion. For these reasons, there is a limit to the decrease of the protrusion amount (length) of the rear end part of the sensor element.

SUMMARY OF THE INVENTION

It is alternatively conceivable to decrease the protrusion amount (length) by which the front end part of the sensor element protrudes toward the front from the front end of the holder for the length reduction of the sensor element. However, there is a need for the detection portion (detection electrodes) to be readily exposed to the gas under measurement for improved detection performance. It is thus not favorable to decrease the protrusion amount (length) of the front end part of the sensor element in terms of detection performance. Further, the lateral cross section (shape and dimensions) of the axial through hole of the holder is adjusted such that the sensor element is inserted through the axial through hole of the holder with almost no clearance left therebetween for stable positioning and holding of the sensor element with a sealing material. As the porous protection layer is formed with a relatively large thickness of e.g. 0.2 to 0.3 mm on the predetermined surface region from the front end of the sensor element toward the rear, the rear end part of the sensor element needs to be inserted through the axial through hole of the holder from the front end side. It is also unfavorable to decrease the region (axial length) of formation of the porous protection layer for assured protection of the sensor element. For these reasons, there is a difficulty in the decrease of the protrusion amount (length) of the front end part of the sensor element.

The present invention has been made to solve the above-mentioned problems. It is an object of the present invention to provide a gas sensor having an improved mounting structure capable of mounting a sensor element so as to reduce the axial length of the sensor element, without causing decrease in protrusion length and deterioration in detection performance, and secure a required region (axial length) for formation of a porous protection layer on a front end part of the sensor element.

According to one aspect of the present invention, there is provided a gas sensor comprising: a cylindrical metal shell arranged in an axial direction of the gas sensor; a holder placed in the metal shell and formed with an axial through hole; and an elongated plate-shaped or rod-shaped sensor element inserted through the axial through hole of the holder with a front end of the sensor element protruding toward the front from a front end face of the holder, the sensor element having, at a front end part thereof, a detection portion covered with a porous protection layer, the porous protection layer being formed on a predetermined region from the front end of the sensor element toward the rear and having a rear end located on or at a front side with respect to a front end of the axial through hole of the holder, wherein the holder has a recessed portion formed in a region enclosing the axial through hole when viewed from the front end face of the holder; wherein the recessed portion is recessed toward the rear from the front end face of the holder; and wherein the sensor element passes through the recessed portion such that the rear end of the porous protection layer is situated within the recessed portion of the holder and is located at a rear side with respect to the front end face of the holder while leaving a space between an inner circumferential surface of the recessed portion and an outer circumferential surface of the porous protection layer.

In the above gas sensor, the sensor element is inserted through the holder such that the rear end of the porous protection layer is situated within the recessed portion of the holder. This allows, even when the region (axial length) of formation of the porous protection layer of the sensor element is the same as those of conventional sensor elements, a decrease in the protrusion length by which the front end of the sensor element protrudes from the front end face of the holder. The total length of the sensor element can be reduced with such a decrease in protrusion length so as to decrease not only the amount of use of noble metal material (e.g. platinum) used in the sensor element and but also the power consumption of the sensor element. In addition, the front end part of the sensor element protruding from a bottom surface of the recessed portion (i.e. the front end of the axial through hole of the holder) is in a state capable of being exposed to a gas under measurement even though partially located within the recessed portion. The length of such a front end part of the sensor element protruding from the bottom surface of the recessed portion corresponds to the protrusion length of front end parts of conventional sensor elements. The rate of exposure of the detection portion of the sensor element to the gas under measurement can be controlled to the same level or close to those of conventional sensor elements, so as not to cause deterioration in detection performance, by setting the bottom surface (lateral cross section) of the recessed portion as large as possible and securing the length of the front end part of the sensor element protruding from the bottom surface of the recessed portion as large as the protrusion length of front end parts of conventional sensor elements. By the above improved mounting structure, it is possible to reduce the total length of the sensor element without causing deterioration in detection while securing the required region (axial length) for formation of the protection layer on the front end part of the sensor element.

Although the rear end of the porous protection layer can be located on the front end of the axial through hole, it is preferable that the rear end of the porous protection layer is located apart from the front end of the axial through hole for the purpose of preventing interference or collision between the porous protection layer and the holder during assembling of the gas sensor by insertion of the sensor element into the axial through hole.

Preferably, the gas sensor may have the feature (A) that: both of an outer circumferential surface of the holder and the inner circumferential surface of the recessed portion are circular in shape when viewed from the front end face of the holder.

As mentioned above, the lateral cross section (shape and dimensions) of the axial through hole of the holder is made substantially the same as the lateral cross section of the sensor element such that the sensor element is inserted through the axial through hole with almost no clearance (or slight clearance) left therebetween for stable positioning and holding of the sensor element. In the case where the sensor element is elongated plate-shaped (rectangular bar-shaped) and rectangular in cross section, the axial through hole is formed with a rectangular opening of substantially the same dimensions as the sensor element. In the case where the sensor element is rod-shaped and circular in cross section, the axial through hole is formed with a circular opening of substantially the same diameter as the sensor element. On the other hand, the holder itself is generally formed of a ceramic material in view of electrical insulation and heat resistance. The holder (except the axial through hole) has e.g. a columnar outer shape such that, when viewed from the front end face, the outer circumferential surface of the holder is circular in shape. It is therefore possible by the adoption of the feature (A) to secure uniformity in wall thickness and effectively prevent the ceramic material from sintering distortion or stress concentration during production of the holder.

It is alternatively feasible to form the recessed portion such that the inner circumferential surface of the recessed portion is polygonal in shape when viewed from the front end face. In this case, the inner circumferential surface of the recessed portion is preferably formed into a polygonal shape having as many sides as possible and thereby being as close as possible to a circle for uniformity in wall thickness.

The gas sensor may also preferably have, in addition to the feature (A), the feature (B): that the gas sensor further comprises a multi-layer protector attached to the metal shell so as to surround the front end part of the sensor element while maintaining a space between the multi-layer protector and the front end part of the sensor element; the multi-layer protector includes an inner protector member located on an innermost side thereof and an outer protector member located outside with respect to the inner protector member; the inner protector member has a cylindrical wall in which vent holes are formed at a position corresponding to the porous protection layer in the axial direction; the outer protector member has a cylindrical wall arranged to cover the vent holes of the inner protector member; and the gas sensor satisfies the condition of D1>D2 where D1 is an inner diameter of the cylindrical wall of the inner protector member at the position corresponding to the porous protection layer in the axial direction; and D2 is an inner diameter of the recessed portion.

For the length reduction of the sensor element, it is preferable to increase the depth of the recessed portion (i.e. the depth by which the recessed portion is recessed from the front end face of the holder) and locate the rear end of the porous protection layer as deep (rear) as possible in the recessed portion. On the other hand, the protector is attached to the metal shell so as to protect the front end part of the sensor element. In recent years, the protector is formed with a multi-layer structure (in general, double-layer structure) for improved protection performance. In view of detection performance, it is preferable that the gas under measurement flows smoothly throughout the inside of the protector, without being built up in the inside of the protector, and comes into contact with the protruding front end part (detection portion) of the sensor element. In the case where the inner circumferential surface of the recessed portion and the inner circumferential surface of the protector are cylindrical in shape, the dimensional condition of D1 (the inner diameter of the protector)<D2 (the inner diameter of the recessed portion) means that the space inside the protector becomes wider toward the bottom of the recessed portion (i.e. toward the rear). This makes it likely that the gas will be built in the deep bottom region of the recessed portion, which may cause deterioration in detection performance. It is thus preferable to set the inner diameter D2 of the recessed portion as large as possible but smaller than the inner diameter D1 of the protector. Further, the detection portion of the sensor element can be effectively protected from water as the vent holes of the inner protector member, which are formed at the position corresponding to the porous protection layer, are covered with the outer protector member. It is therefore possible by the adoption of the feature (B) to effectively protect the detection portion of the sensor element from water contained in the gas under measurement, while allowing smooth introduction of the gas under measurement to the detection portion of the sensor element, and then, effectively prevent breakage of the sensor element as well as detection performance deterioration of the sensor element.

The gas sensor may preferably have, in addition to the feature (B), the feature (C): that the metal shell has an annular front end portion formed with an in inner diameter smaller than an outer diameter of the holder and an annular step surface located at a rear side with respect to an inner circumferential surface of the annular front end portion; the holder is placed in position within the metal shell by engagement of the front end face of the holder on the annular step surface of the metal shell; and the gas sensor satisfies the condition of D3>D2 where D3 is the inner diameter of the annular front end portion.

It is possible by the adoption of the feature (C) to effectively secure the radial thickness of the recessed portion of the holder for improvement in strength.

Further, the gas sensor may preferably have the feature (D): the front end of the sensor element protrudes toward the front from a front end of the metal shell; and the gas sensor satisfies the condition of L5>L3 where L5 is a protrusion length by which the front end of the sensor element protrudes toward the front from the front end of the metal shell; and L3 is a length by which the rear end of the porous protection layer is located at the rear side with respect to the front end face of the holder.

By the adoption of the feature (D), it is possible to effectively increase the length by which the front end of the sensor element protrudes toward the front from the front end of the metal shell for fast response for gas concentration detection (measurement).

The other objects and features of the present invention will also become understood from the following description.

DESCRIPTION OF THE EMBODIMENTS

The present invention will be described below with reference to FIGS. 1 to 10. The following embodiment specifically refers to, as a gas sensor 1, a wide range oxygen sensor mounted on an exhaust pipe of an internal combustion engine and adapted to detecting the concentration of oxygen in an exhaust gas (as a gas under measurement) flowing through the exhaust pipe.

First, the overall structure of the gas sensor 1 will be explained below.

Figure 1:
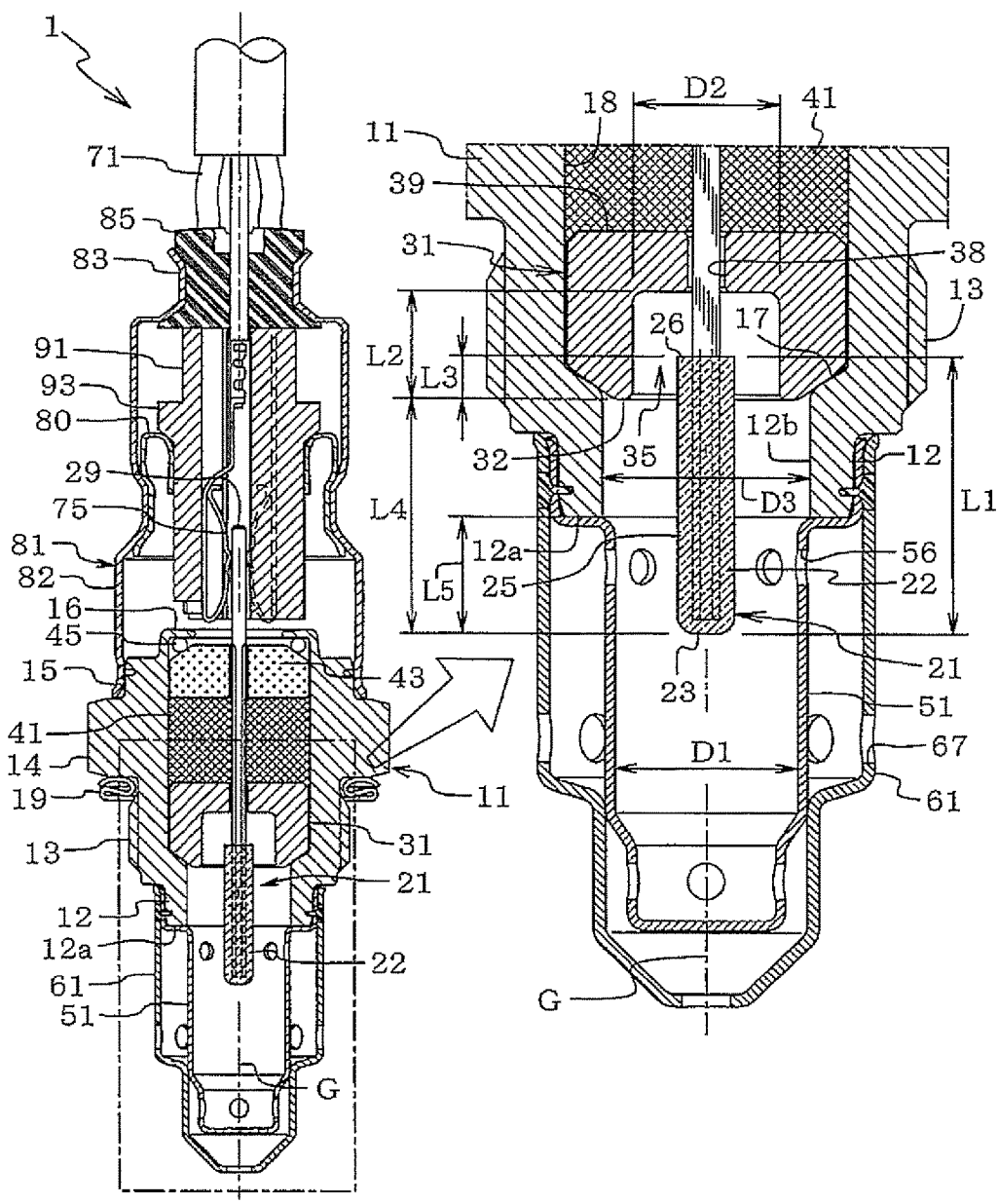
FIG. 1 is a cross-sectional view with a partial enlarged section of a gas sensor according to one embodiment of the present invention.

As shown in FIG. 1, the gas sensor 1 includes a cylindrical metal shell (metal housing) 11 arranged in an axial direction of the gas sensor 1, a holder 31 placed in the metal shell 11 and formed with an axial through hole 38 and an elongated plate-shaped sensor element 21 inserted through the axial through hole 38 of the holder 31. A front end 23 and its vicinity (referred to as "front end part") of the sensor element 21 protrudes toward the front from a front end face (front end) 32 of the holder 31. A detection portion 22 is formed on the front end part of the gas sensor 1. A seal material 41 (such as talc), a pushing ring 43 (such as sleeve of insulating material) and a ring washer 45 are placed in this order on a rear end face 39 of the holder 31 within the metal shell 11 so that, when the seal material 41 is axially compressed by pushing the pushing ring 43 and the ring washer 45, the sensor element 21 is hermetically fixed by the holder 31 in the metal shell 11 via the seal material 41, the pushing ring 43 and the ring washer 45. A rear end 29 and its vicinity (referred to as "rear end part") of the sensor element 21 protrudes toward the rear from the pushing ring 43 and from the metal shell 11. Electrode terminals (not shown) are formed on the rear end part of the sensor element 21 and respectively electrically connected to front ends of leads 71 by crimp contacts 75. The gas sensor 1 also includes a double-layer protector (as a multi-layer protector; explained later in detail) attached to the metal shell 11 so as to protect therein the front end part of the sensor element 21 and a protection tube 81 attached to the metal shell 11 so as to protect therein the rear end part of the sensor element 21 (including the electrode terminals). The leads 71 are drawn to the outside from a rear end of the protection tube 81 through a seal member 85.

Next, the respective structural components of the gas sensor 1 will be explained in more detail below.

The sensor element 21 is formed into an elongated, rectangular cross-section plate shape in the axial direction. The detection portion 22 is provided on the front end part of the sensor element 21 and exposed to the gas under measurement to detect the specific gas component in the gas under measurement. In the present embodiment, the sensor element 21 is predominantly composed of ceramic and solid electrolyte and is of known configuration. More specifically, the sensor element 21 has a solid electrolyte material (member) laminated on a ceramic material (substrate) and a pair of detection electrodes (not shown) formed on a front end side of the solid electrolyte material so as to constitute the detection portion 22. The sensor element 21 also has a porous protection layer 25 formed of a porous material e.g. alumina or spinel on a predetermined region L1 from the front end 23 toward the rear so as to cover the detection portion 22 with the porous protection layer 25. Herein, the lateral cross section of the region L1 of the sensor element 21 on which the porous protection layer 25 is formed is larger by a thickness of the porous protection layer 25 (e.g. 0.2 to 0.3 mm) than that of the remaining region of the sensor element 21 located at the rear side with respect to the porous protection layer 25. (In the drawings, the thickness of the porous protection layer 25 is exaggerated for purposes of illustration.) Further, the lateral cross section of the region of the sensor element 21 located at the rear side with respect to the porous protection layer 25 is of uniform rectangular shape throughout its length (see FIGS. 3 and 4). The sensor element 21 further includes a heater (not shown) embedded in the ceramic material so as to correspond in position to the detection portion 22. The electrode terminals are formed on the rear end part of the sensor element 21 and connected to the respective leads 71 for signal output from the detection portion 22 and for energization to the heater. Although not shown in the drawings, the electrode terminals are generally elongated rectangular in shape. Two or three electrode terminals are arranged side by side on each of opposite plate surfaces of the rear end part of the sensor element 21.

The metal shell 11 is formed into a different-diameter cylindrical shape in the axial direction and includes a cylindrical (annular) front end portion 12 formed with a small diameter and around which the double-layer protector is fixed by welding. A thread 13 of larger outer diameter than the front end portion 12 is made on an outer circumferential surface of the metal shell 11 at a rear position with respect to the front end portion 12. The metal shell 11 also includes a polygonal portion 14 located at the rear side with respect to the thread 13 for mounting the gas sensor 1 onto the exhaust pipe by screwing the thread 13 into the mounting hole, a cylindrical portion 15 located at the rear side with respect to the polygonal portion 14 and around which the protection tube 81 is fixed by welding and a cylindrical rear end portion 16 located at the rear side with respect to the cylindrical portion 15 and made smaller in outer diameter than the cylindrical portion 15 and smaller in thickness for crimping. In FIG. 1, the rear end portion 16 of the metal shell 11 is radially inwardly bent by crimping. On the other hand, the metal shell 11 has an inner circumferential surface 12b located adjacent to a front end 12a of the front end portion 12, an inner circumferential surface 18 formed with an enlarged uniform inner diameter at a rear position with respect to the inner circumferential surface 12b and an annular tapered step surface 17 located between the inner circumferential surfaces 12b and 18 and decreasing in diameter toward the front. A gasket 19 is fitted on a front surface of the polygonal portion 14 so as to, when the gas sensor 1 is mounted on the exhaust pipe, provide a seal the gas sensor 1 and the exhaust pipe.

The holder 31 is formed of an insulating material e.g. alumina in a substantially cylindrical shape and is placed in the metal shell 11. An outer circumferential edge surface 32b of the holder 32 located adjacent to the front end face 32 is tapered so as to decrease in diameter toward the front so that the holder 31 is placed in position within the metal shell 11 by engagement of the outer circumferential edge surface 32b of the holder 21 on the annular step surface 17 of the metal shell 11 (see FIG. 2). An outer circumferential surface 34 of the holder 31 is clearance-fitted in the inner circumferential surface 18 of the metal shell 11.

The axial through hole 38 is formed through the center of the holder 31 in alignment with an axis G of the metal shell 11 and has a rectangular opening of substantially the same dimensions as those of the lateral cross section of the region of the sensor element 21 located at the rear side with respect to the porous protection layer 25 such that the region of the sensor element 21 located at the rear side with respect to the porous protection layer 25 can be inserted through the axial through hole 38 with almost no clearance left therebetween.

The holder 31 also has a recessed portion 35 formed in a region of the front end face 32 enclosing the axial through hole 38 and recessed by a predetermined depth L1 toward the rear from the front end face 32. In the present embodiment, the recessed portion 35 is circular in shape when viewed from the front end face 32 and has an inner circumferential surface 36 coaxial with the outer circumferential surface 34 of the holder 31 (see FIGS. 5 to 7). An inner diameter D2 of the recessed portion 35 is set in such a manner that the front end part of the sensor element 21 passes through the recessed portion 35 while maintaining a space K between the inner circumferential surface 36 of the recessed portion 35 and the front end part of the sensor element 21 (protection layer 25) (see FIGS. 2, 5 and 6). On the other hand, the inner diameter D2 of the recessed portion 35 is set smaller than, but close to, an inner diameter D1 of the double-layer protector and an inner diameter D3 of the front end portion 12 of the metal shell 11 that is smaller than an outer diameter of the holder 31 (see FIGS. 1 to 7). A bottom surface 37 of the recessed portion 35 (corresponding to a front end of the axial through hole 38) is made flat.

Figure 2:
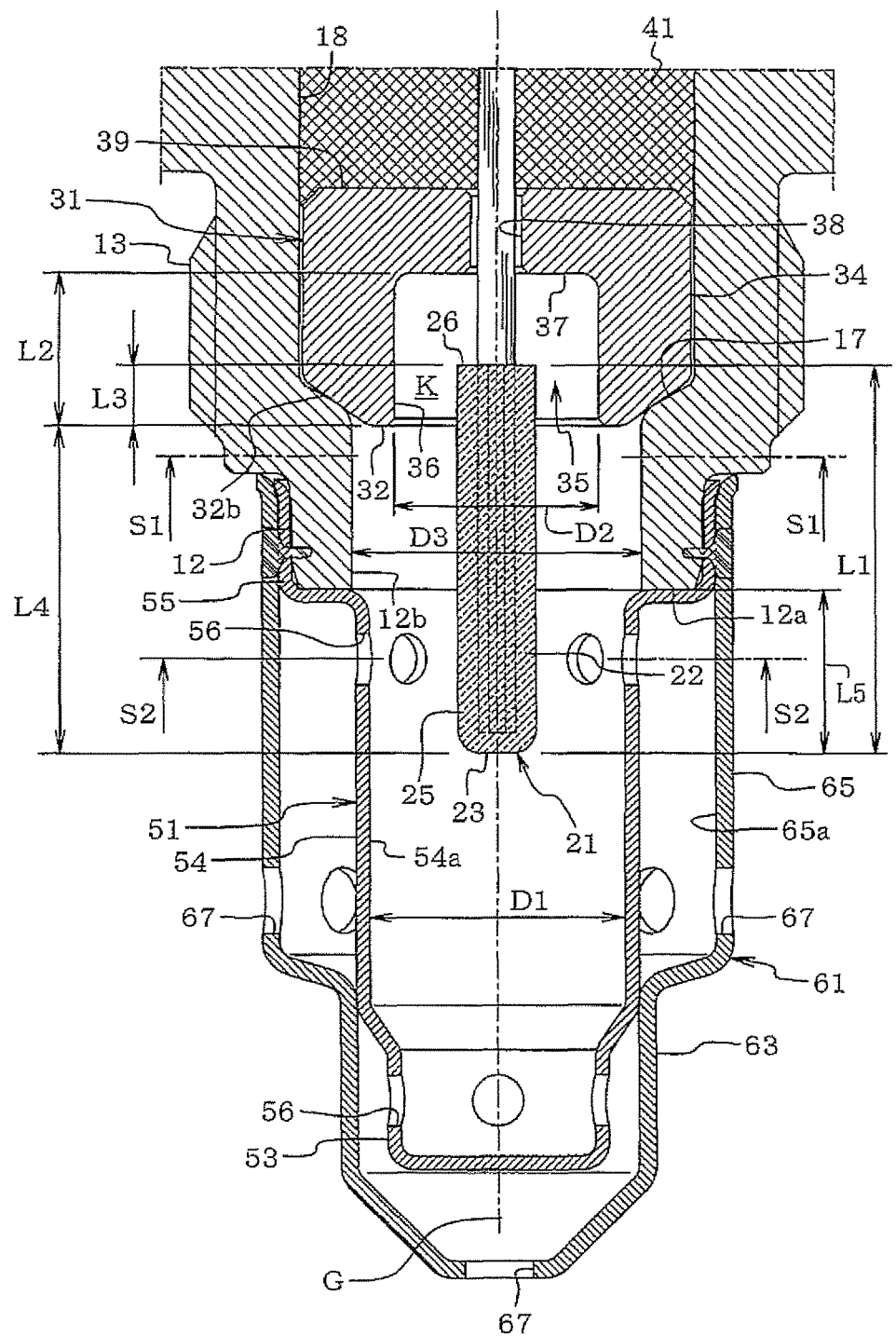
FIG. 2 is an enlarged cross-sectional view of substantive part of the gas sensor of FIG. 1.
Figure 3:
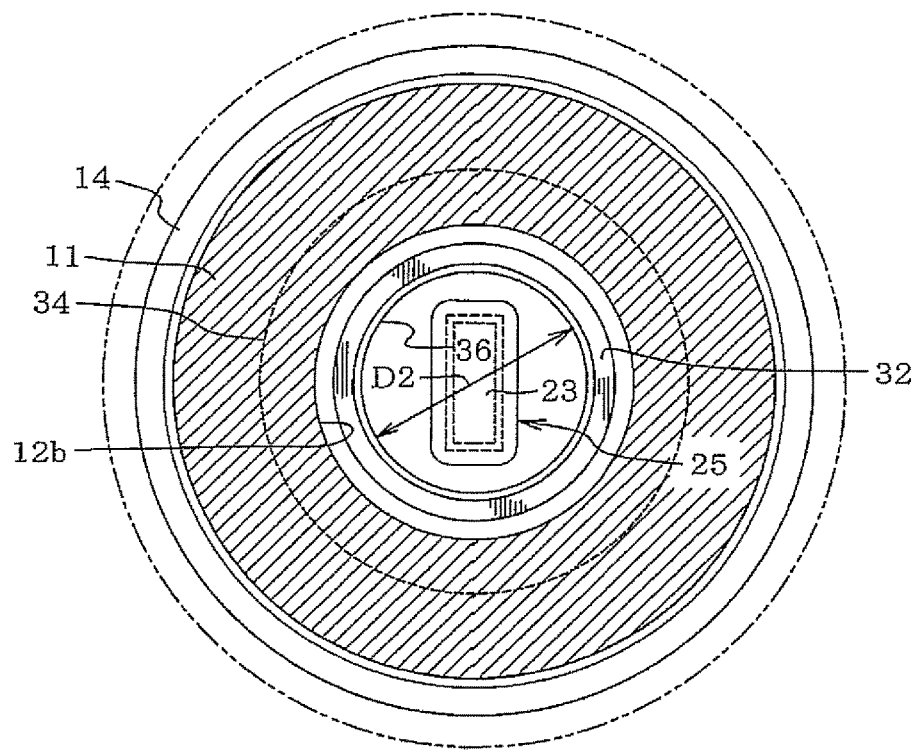
FIG. 3 is a cross-sectional view of the gas sensor of FIG. 1, taken along line S1-S1 of FIG. 2.
Figure 4:
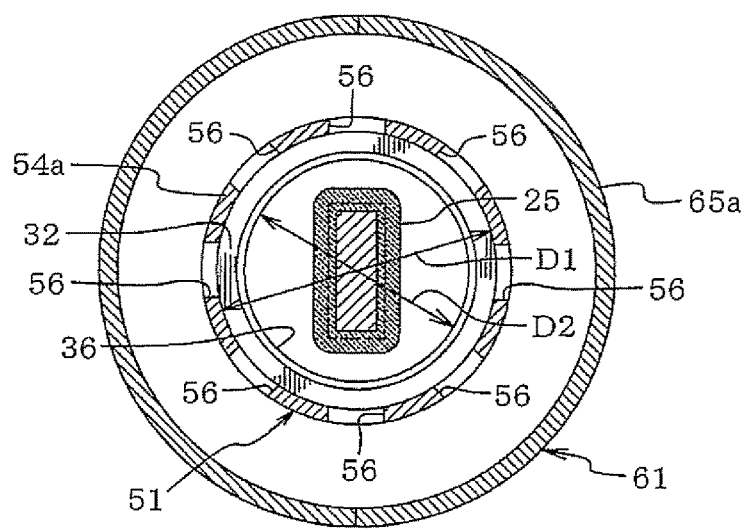
FIG. 4 is a cross-sectional view of the gas sensor of FIG. 1, taken along line S2-S2 of FIG. 2.
Figure 5:
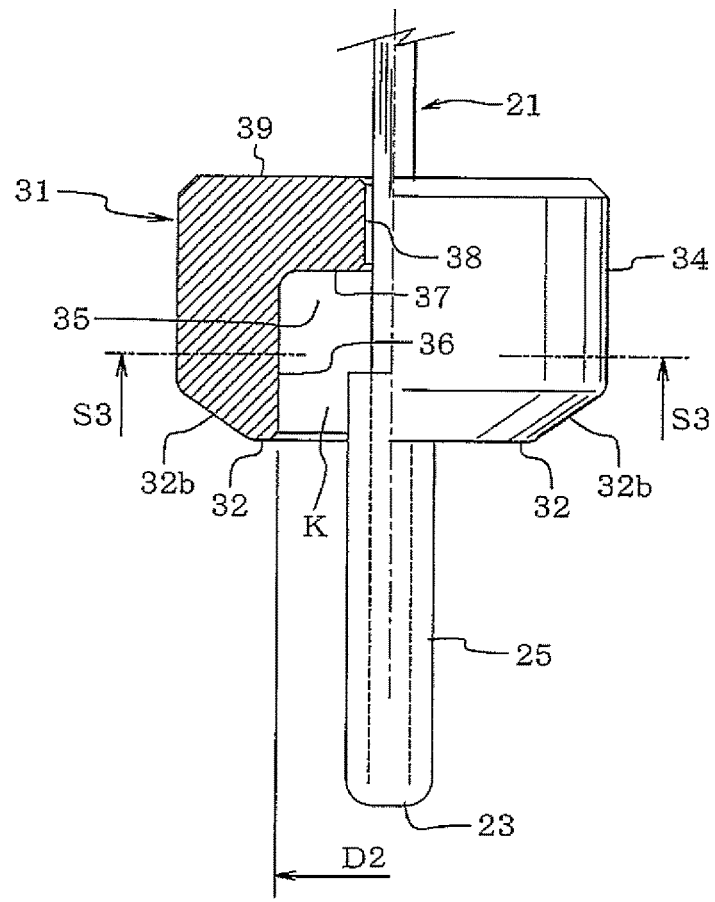
FIG. 5 is a half cross-sectional view of the state of insertion of a sensor element through a through hole of a holder in the gas sensor of FIG. 1.
Figure 6:
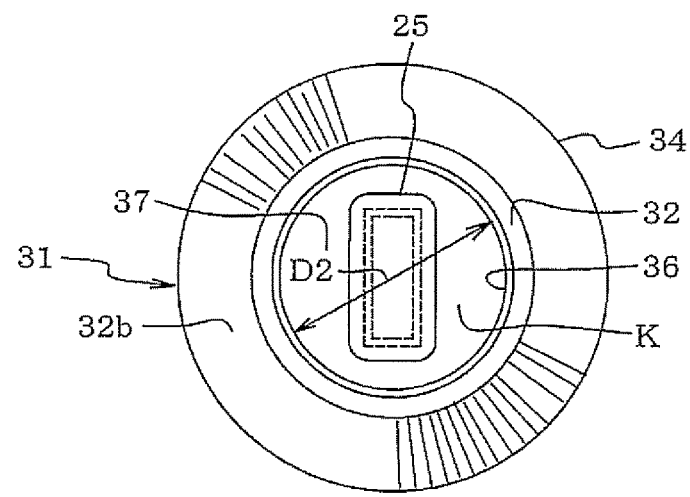
FIG. 6 is a schematic view of the gas sensor of FIG. 1, as viewed from the bottom of FIG. 5.
Figure 7:
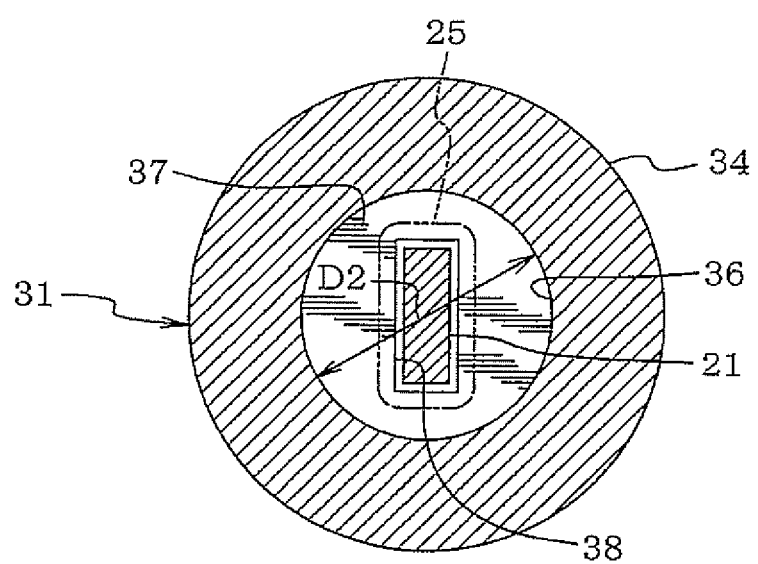
FIG. 7 is a cross-sectional view of the gas sensor of FIG. 1, taken along line S3-S3 of FIG. 5.

In the present embodiment, the sensor element 21 is inserted through the axial through hole 38 of the holder 31, with the front end 23 of the sensor element 21 protruding toward the front from the front end face 32 of the holder 31 and from the front end 12a of the metal shell 11, as shown in FIGS. 1 and 2. In particular, a rear end 26 and its vicinity of the porous protection layer 25 is situated within the recessed portion 35; and the rear end 26 of the porous protection layer 25 is located at the rear side with respect to the front end (front end face 32) of the holder 31 by an appropriate length L3 (see FIG. 2).

With such a structure, the protrusion length L4 by which the front end 23 of the sensor element 21 protrudes toward the front from the front end 32 of the holder 31 can be decreased (as will be explained in detail later) even when the axial length L1 of the porous protection layer 25 of the sensor element 21 is the same as those of conventional sensor elements. As the protrusion length L4 is decreased by the amount that the rear end 26 of the porous protection layer 25 is situated within the recessed portion 35, it is possible to reduce the total length of the sensor element 21. For the length reduction of the sensor element 21, it is effective to locate the rear end 26 of the porous protection layer 25 closer to the bottom surface 37 of the recessed portion 35 (i.e. the front end of the axial through hole 38). The rear end 26 of the porous protection layer 25 can be thus located on the same position as the bottom surface 37 of the recessed portion 35 (i.e. located on the front end of the axial through hole 38). Further, it is preferable to set the protrusion length L5 by which the front end 23 of the sensor element 21 protrudes toward the front from the front end 12a of the metal shell 11 larger than the protrusion length L3 by which the rear end 26 of the porous protection layer 25 is located at the rear side with respect to the front end face 32 of the holder 31 for fast response for gas concentration detection (measurement).

In the gas sensor 1, the sensor element 21 is hermetically fixed by the holder 31 in the metal shell 11 via the seal material 41, the pushing ring 43 and the ring washer 45 by crimping the rear end portion 16 of the metal shell 11 radially inwardly toward the front and thereby compressing the seal material 41 axially through the pushing ring 43 and the ring washer 45 as mentioned above.

Referring back to FIG. 1, the front end part of the sensor element 21 is covered with the double-layer protector. The double-layer protector includes an inner protector member (protection tube) 51 located on an inner (innermost) side thereof and an outer protector member (protection tube) 61 located outside with respect to the inner protector member 51 as shown in FIGS. 1 and 2.

The inner protector member 51 has a bottomed cylindrical shape enlarged in diameter in three stages from the front toward the rear. A large-diameter cylindrical rear end portion 55 of the inner protector member 51 is fitted around and welded to the front end portion 12 of the metal shell 11 (see FIG. 2). A middle-diameter cylindrical portion 54 of the inner protector member 51 has a cylindrical wall 54a axially uniform in diameter and longer in length than a small-diameter cylindrical front end portion 53 of the inner protector member 51. A plurality of circumferentially spaced vent holes 56 (e.g. eight vent holes) are formed in a rear end side of the cylindrical wall 54a at a position axially corresponding to the porous protection layer 25 on the front end part of the sensor element 21. The inner diameter D1 of the cylindrical wall 54a of the middle-diameter cylindrical portion 54 (i.e. the inner diameter of the double-layer protector) is set equal to or smaller than the inner diameter D3 of the front end portion 12 of the metal shell 11, but is set larger than the inner diameter D2 of the recessed portion 35 of the holder 31 as mentioned above. A plurality of circumferentially spaced vent holes 56 (e.g. four vent holes) are also formed in the front end portion 53.

The outer protector member 61 has a bottomed cylindrical shape enlarged in diameter in two stages from the front toward the rear. A large-diameter cylindrical rear portion 65 of the outer protector member 61 is fitted around the rear end portion 55 of the inner protector member 51 and welded to the front end portion 12 of the metal shell 11. An inner diameter of the rear portion 65 of the outer protector member 61 is set equal to an outer diameter of the rear end portion 55 of the inner protector member 51. An axial length of the rear portion 65 is set in such a manner that a front end of the rear portion 65 axially corresponds in position to a front end and its vicinity of the middle-diameter cylindrical portion 54. A cylindrical wall 65a of the rear portion 65 is arranged so as to cover some of the vent holes 56 of the inner protector member 51 axially corresponding in position to the porous protection layer 25. A plurality of circumferentially spaced vent holes 67 (e.g. eight vent holes) are formed in a front end side of the rear portion 55. A vent hole 67 is also formed in the center of a front end of the outer protector member 61. A small-diameter cylindrical front portion 63 of the outer protector member 61 has a rear end fitted around the front end of the middle-diameter cylindrical portion 54. By this arrangement, the exhaust gas flows from the upstream side of the exhaust pipe into the inside of the double-layer protector through the vent holes 67 of the outer protector member 61 and though the vent holes 56 of the inner protector member 51, reaches the front end part of the sensor element 21, and then, flows out to the downstream side of the exhaust pipe though the vent holes 56 of the inner protector member 51 and through the vent holes 67 of the outer protector member 61.

As also shown in FIG. 1, the crimp contacts 75 are attached to the front ends of the leads 71 and crimped onto the electrode terminals 24 of the sensor element 21 under their respective spring action so as to make electrical connection between the electrode terminals and the leads 71. In the present embodiment, a crimp contact holding member 91 of ceramic material is placed in the protection tube 81. Crimp contact accommodation holes are formed in the crimp contact holding member 91 such that the crimp contacts 75 are held in an opposed arrangement through the respective crimp contact accommodation holes. Further, an annular supporting member 80 is fixed in the protection tube 81 so as to restrict radial or frontward movement of the crimp contact holding member 91.

The protection tube 81 is formed of a metal material in a different-diameter cylindrical shape. A large-diameter cylindrical front end portion 82 of the protection tube 81 is fitted around and welded to the cylindrical portion 15 of the metal shell 11 so that the rear end part of the gas sensor 1 is hermetically covered by the protection tube 81

The seal member 85 is formed of e.g. a rubber material and fitted in a small-diameter cylindrical rear end portion 83 of the protection tube 81. Lead insertion holes are formed in the seal member 85 such that the leads 71 are drawn to the outside through the respective lead insertion holes. The seal member 85 is compressed by radially inwardly crimping the small-diameter cylindrical rear end portion 83 of the protection tube 81 so as to hermetically close the rear end opening of the outer tube 81.

Herein, the seal material 85 is arranged so as to push a rear end of the crimp contact holding member 91 toward the front for stable positioning of the crimp contact holding member 91 and the crimp contacts 75. A flange portion 93 is formed on an outer circumference of the crimp contact holding member 91 and supported on the annular supporting member 80 within the protection tube 81 such that the crimp contact holding member 91 receives a compressive force from the seal material 85.

As mentioned above, the gas sensor 1 of the present embodiment is characterized in that: the recessed portion 35 is formed in the region of the front end face 32 enclosing the axial through hole 38 and recessed toward the rear from the front end face 32; and the sensor element 21 passes through the recessed portion 35 such that the rear end 26 of the porous protection layer 25 is situated within the recessed portion 35 and is located at the rear side with respect to the front end face 32 of the holder 31 while maintaining a space K between the inner circumferential surface 36 of the recessed portion 35 and the outer circumferential surface of the porous protection layer 25. (see FIGS. 2, 5 and 6). This allows, even when the axial length L1 of the porous protection layer 25 of the sensor element 21 is the same as those of conventional sensor elements, the protrusion length L4 by which the front end 23 of the sensor element 21 protrudes from the front end face 32 of the holder 31 to be decreased by the amount that the rear end 26 of the porous protection layer 25 is situated within the recessed portion 35. The total length of the sensor element 21 can be thus reduced with such a decrease in protrusion length so as to achieve cost reduction and energy conservation.

In addition, the front end part of the sensor element 21 protruding from the bottom surface 37 of the recessed portion 35 (i.e. the front end of the axial through hole 38) is in a state capable of being exposed to the exhaust gas (gas under measurement) even though partially located within the recessed portion 35. In the present embodiment, the length of such a front end part of the sensor element 21 protruding from the bottom surface of the recessed portion 35 corresponds to the protrusion length of front end parts of conventional sensor elements. The rate of exposure of the detection portion 22 of the sensor element 21 to the exhaust gas (gas under measurement) can be controlled to the same level or close to those of conventional sensor elements, so as not to cause deterioration in detection performance, by setting the bottom surface 37 (lateral cross section) of the recessed portion 35 as large as possible and securing the length of the front end part of the sensor element protruding from the bottom surface of the recessed portion as large as the protrusion length of front end parts of conventional sensor elements.

By the above improved mounting structure, it is possible to reduce the total length of the sensor element 21 without causing deterioration in detection while securing the required region for formation of the porous protection layer 25 on the front end part of the sensor element 21.

Furthermore, the inner and outer protector members 51 and 61 are attached to the front end portion 12 of the metal shell 11 such that the vent holes 56 formed in the cylindrical wall 54a of the inner protector member 51 at the position axially corresponding to the porous protection layer 25 are covered with the cylindrical wall 65a of the outer protector member 61. The detection portion 22 of the sensor element 21 can be thus effectively protected from water contained in the exhaust gas (gas under measurement). As the vent holes 56 are formed in the cylindrical wall 54a of the inner protector member 51 at the position axially corresponding to the porous protection layer 25, the exhaust gas (gas under measurement) flowing in the inside of the outer protector member 61 can be smoothly introduced to and brought into contact with the detection portion 25 through the vent holes 56 of the inner protector member 51. It is thus possible to effectively prevent breakage of the sensor element 21 caused due to thermal impact by the adhesion of water as well as detection performance deterioration of the sensor element 21.

It is further possible to effectively prevent the exhaust gas (gas under measurement) from being built up in the recessed portion 35 inside the inner protector member 51 and thereby possible to favorably improve the detection performance of the sensor element 21 by satisfaction of the dimensional condition of D1>D2 where D is the inner diameter of the cylindrical wall 54a of the inner protector member 51 at the position corresponding to the porous protection layer 25; and D2 is the inner diameter of the inner circumferential surface 36 the recessed portion 35.

The manufacturing of the above-structured gas sensor 1 (including the mounting of the sensor element 21) will be explained below.

Figure 8:
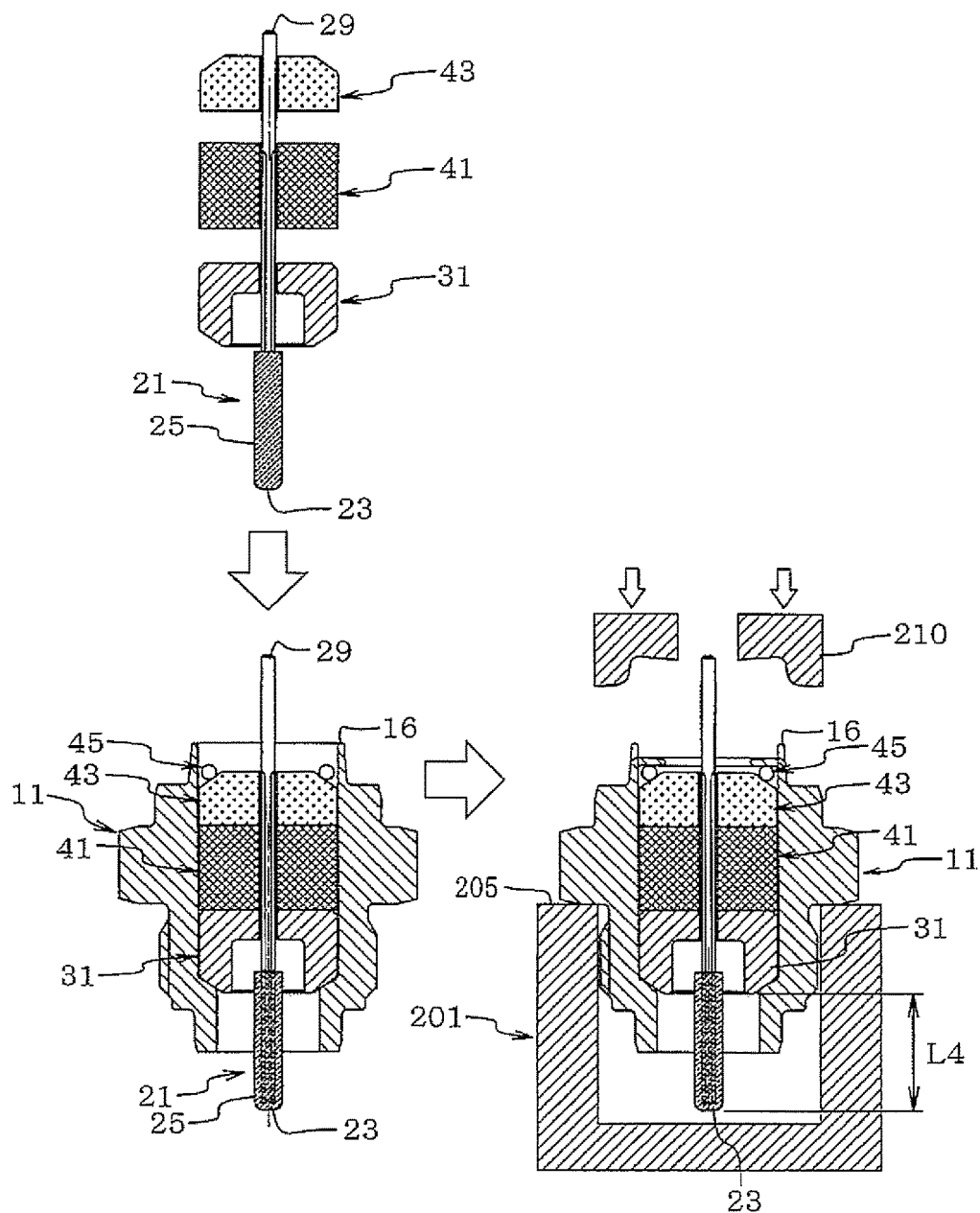
FIG. 8 is a schematic view showing a step of fixing the sensor element to a metal shell during manufacturing of the gas sensor of FIG. 1.

As shown in the upper-left side of FIG. 8, the rear end part of the sensor element 21 is inserted through the holder 31, the seal material 41 and the pushing ring 43. The resulting subassembly unit is inserted and placed in the metal shell 11 as shown in the lower-left side of FIG. 8. The ring washer 45 is arranged on a rear end of the pushing ring 43 within the inside of the rear end portion 16 of the metal shell 11. At this stage, the front end 23 of the sensor element 21 protrudes by an appropriate amount (length).

Then, the metal shell 11 is placed and held in position win a jig 201 as shown in the right side of FIG. 8 by contact of a front-facing surface of the polygonal portion 14 of the metal shell 11 with a positioning portion 205 of the jig 201. When the rear end portion 16 of the metal shell 11 is bent and crimped radially inwardly toward the front by a crimping die 210, the seal material 41 and the pushing ring 43 are axially compressed to push the holder 31 in which the sensor element 21 is inserted. Thus, the sensor element 21, the holder 31 etc. are fixed in the metal shell 11 with the front end 23 of the sensor element 21 protruding by the length L4 from the front end face 32 of the holder 31. It is noted that, although not specifically shown in the drawings, each of the seal material 41 and the insulating sleeve 43 has an elongated rectangular hole corresponding in shape to the lateral cross section of the sensor element 21 (as viewed in the direction of the axis G), before the compression, as in the case of the holder 31.

Figure 9:
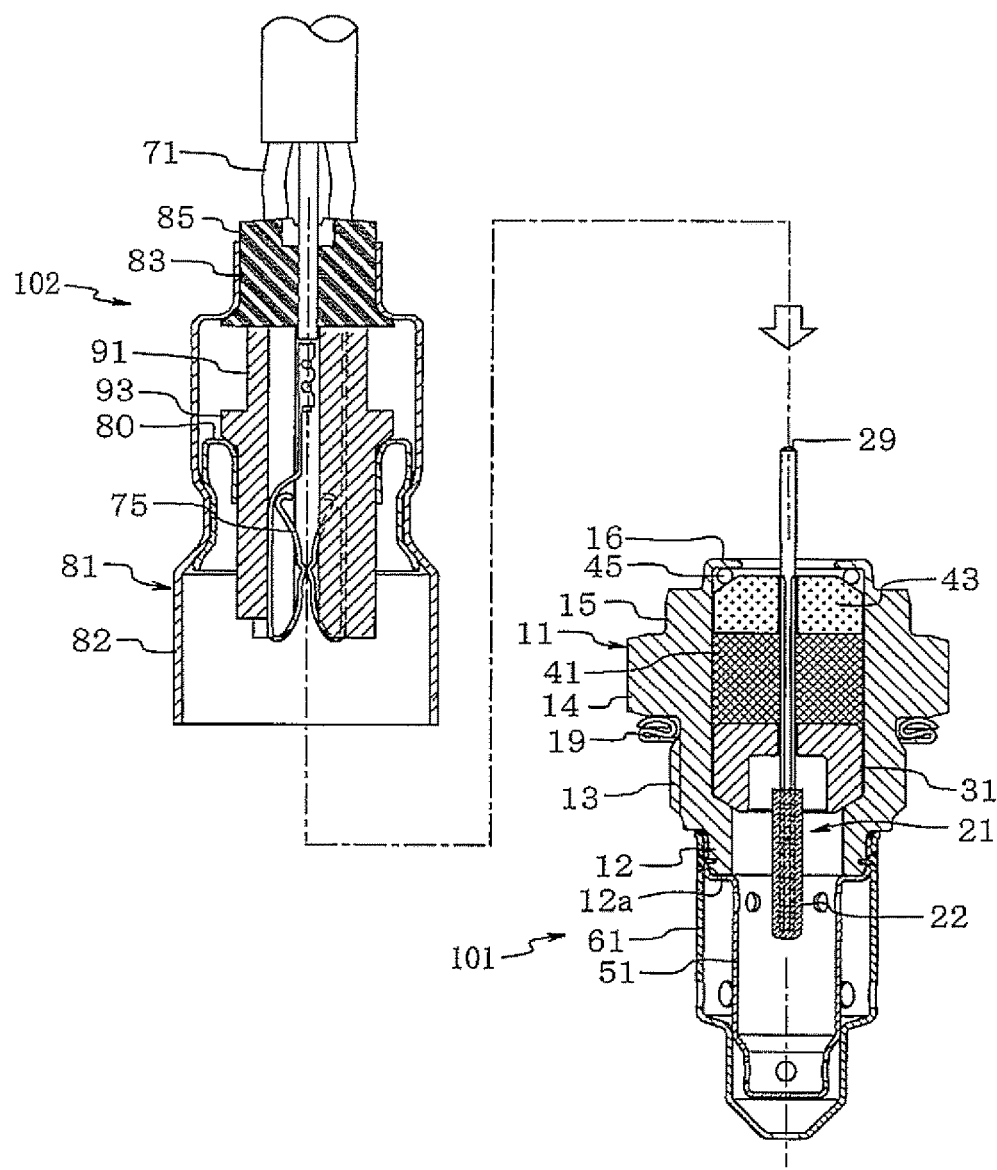
FIG. 9 is a schematic view showing a final assembling step during manufacturing of the gas sensor of FIG. 1.

As shown in FIG. 9, the above-obtained subassembly unit is processed into a front-side subassembly unit 101 by welding the protector members 51 and 61 to the metal shell 11 and fitting the gasket 19 on the metal shell 11; whereas a rear-side subassembly unit 102 is obtained by assembling the other respective sensor structural components together. These subassembly units 101 and 102 are combined together by arranging the subassembly units 101 and 102 coaxially with each other and fitting the subassembly unit 201 into the subassembly unit 102. When the protruding rear end part of the sensor element 21, on which the electrode terminals 24 have been formed, is inserted between the opposed crimp contacts 75 in the crimp contact holding member 91, the crimp contacts 75 are crimped to the electrode terminals 24 under their respective spring action. The large-diameter cylindrical front end portion 82 of the protection tube 81 is fitted around the cylindrical portion 15 of the metal shell 11. The entire circumference of the overlap part between the front end portion 82 of the protection tube 81 and the cylindrical portion 15 of the metal shell 11 is then subjected to laser welding. By this, the gas sensor 1 of FIG. 1 is completed.

The entire contents of Japanese Patent Application No. 2013-106474 (filed on May 20, 2013) and No. 2013-239722 (filed on Nov. 20, 2013) are herein incorporated by reference.

Although the present invention has been described with reference to the above specific embodiment, the present invention is not limited to such a specific embodiment. Various modifications and variations can be made to the above embodiment without departing from the scope of the present invention.

Figure 10:
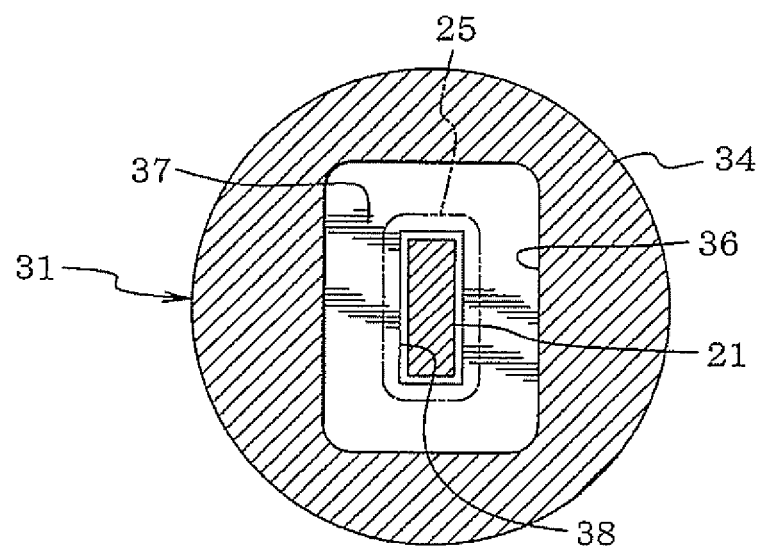
FIG. 10 is a cross-sectional view corresponding to FIG. 5 and showing a modification of the holder in the gas sensor of FIG. 1.

For example, both of the outer circumferential surface 34 of the holder 31 and the inner circumferential surface 36 of the recessed portion 35 are circular in shape when viewed from the front end face 32 in the above embodiment. This leads to uniformity in wall thickness and makes it possible to, when the holder 31 is formed of ceramic, effectively prevent the ceramic material from sintering distortion or stress concentration. The recessed portion 35 may alternatively be formed such that the inner circumferential surface 36 of the recessed portion 35 is polygonal (rectangular) in shape as shown in FIG. 10 when viewed from the front end face 32. In this case, it is favorable to set the shape of the holder 31 (recessed portion 35) so as to secure uniformity in wall thickness for improvement in strength and for prevention of distortion etc.

The shape of the sensor element 21 is not limited to that of the above embodiment. Although the sensor element 21 is rectangular in cross section in the above embodiment, the sensor element 21 may alternatively be shaped into any other cross section such as square cross section. Further, the sensor element 21 may alternatively be formed into a rod shape.

In the above embodiment, the present invention is embodied as the wide range oxygen sensor. The present invention is not however limited to such an oxygen sensor and can be applied to various types of gas sensors.

The scope of the invention is defined with reference to the following claims.

What is claimed is:

1. A gas sensor, comprising:
a cylindrical metal shell arranged in an axial direction of the gas sensor;
a holder placed in the metal shell and formed with an axial through hole; and
an elongated plate-shaped or rod-shaped sensor element inserted through the axial through hole of the holder with a front end of the sensor element protruding toward the front from a front end face of the holder, the sensor element having, at a front end part thereof, a detection portion covered with a porous protection layer, the porous protection layer being formed on a predetermined region from the front end of the sensor element toward the rear and having a rear end located on or at a front side with respect to a front end of the axial through hole of the holder,
wherein the holder has a recessed portion formed in a region enclosing the axial through hole when viewed from the front end face of the holder;
wherein the recessed portion is recessed toward the rear from the front end face of the holder;
wherein the sensor element passes through the recessed portion such that the rear end of the porous protection layer is situated within the recessed portion of the holder and is located at a rear side with respect to the front end face of the holder while maintaining a space between an inner circumferential surface of the recessed portion and an outer circumferential surface of the porous protection layer; and
wherein both of an outer circumferential surface of the holder and the inner circumferential surface of the recessed portion are circular in shape when viewed from the front end face of the holder;

said gas sensor further comprising a multi-layer protector attached to the metal shell so as to surround the front end part of the sensor element while maintaining a space between the multi-layer protector and the front end part of the sensor element, the multi-layer protector including an inner protector member located on an innermost side thereof and an outer protector member located outside with respect to the inner protector member,
wherein the inner protector member has a cylindrical wall in which vent holes are formed at a position corresponding to the porous protection layer in the axial direction;
wherein the outer protector member has a cylindrical wall arranged to cover the vent holes of the inner protector member; and
wherein the gas sensor satisfies the condition of $D1>D2$ where $D1$ is an inner diameter of the cylindrical wall of the inner protector member at the position corresponding to the porous protection layer in the axial direction; and $D2$ is an inner diameter of the recessed portion.

2. The gas sensor according to claim 1,
wherein the metal shell has an annular front end portion formed with an in inner diameter smaller than an outer diameter of the holder and an annular step surface located at a rear side with respect to an inner circumferential surface of the annular front end portion;
wherein the holder is placed in position within the metal shell by engagement of the front end face of the holder on the annular step surface of the metal shell; and
wherein the gas sensor satisfies the condition of $D3>D2$ where $D3$ is the inner diameter of the annular front end portion.

3. The gas sensor according to claim 1,
wherein the front end of the sensor element protrudes toward the front from a front end of the metal shell; and
wherein the gas sensor satisfies the condition of $L5>L3$ where $L5$ is a protrusion length by which the front end of the sensor element protrudes toward the front from the front end of the metal shell; and $L3$ is a length by which the rear end of the porous protection layer is located at the rear side with respect to the front end face of the holder.

* * * * *